US010448835B2

(12) United States Patent
Pierro et al.

(10) Patent No.: US 10,448,835 B2
(45) Date of Patent: Oct. 22, 2019

(54) CONTACTLESS SYSTEM AND METHOD FOR ASSESSING TISSUE VIABILITY AND OTHER HEMODYNAMIC PARAMETERS

(71) Applicants: Vivonics, Inc., Bedford, MA (US); The Board of Trustees of The University of Arkansas, Little Rock, AR (US)

(72) Inventors: Michele Pierro, Westford, MA (US); Kyle Quinn, Fayetteville, AR (US); Alan Woessner, Fayetteville, AR (US)

(73) Assignees: Vivonics, Inc., Bedford, MA (US); The Board of Trustees of The University of Arkansas, Little Rock, AR (US)

( * ) Notice: Subject to any disclaimer, the term of this patent is extended or adjusted under 35 U.S.C. 154(b) by 0 days.

(21) Appl. No.: 16/239,734

(22) Filed: Jan. 4, 2019

(65) Prior Publication Data
US 2019/0223730 A1 Jul. 25, 2019

Related U.S. Application Data

(60) Provisional application No. 62/621,873, filed on Jan. 25, 2018.

(51) Int. Cl.
*A61B 5/00* (2006.01)
*A61B 5/1455* (2006.01)
(52) U.S. Cl.
CPC ............ *A61B 5/0071* (2013.01); *A61B 5/445* (2013.01); *A61B 5/14551* (2013.01)
(58) Field of Classification Search
CPC .... A61B 5/0071; A61B 5/445; A61B 5/14551
See application file for complete search history.

(56) References Cited

U.S. PATENT DOCUMENTS 6,104,939 A 8/2000 Groner et al.
2007/0100246 A1 5/2007 Hyde
(Continued)

OTHER PUBLICATIONS

Written Opinion of the International Searching Authority dated Jul. 18, 2019 for International Application No. PCT/US2019/012323 (six (6) pages total).
(Continued)

*Primary Examiner* — Peter Luong
(74) *Attorney, Agent, or Firm* — Iandiorio Teska & Coleman, LLP

(57) ABSTRACT

A contactless system for assessing tissue viability and other hemodynamic parameters includes one or more light sources configured to emit lights at a predetermined wavelength sensitive to hemoglobin concentration associated with spontaneous hemodynamic oscillations at tissue in a predetermined area of a human subject. One or more polarizers are each coupled to one or more of the one or more light sources and are configured to polarize the light to a polarized state such that the polarized light in the polarized state diffuses into the tissue in the predetermined area at a predetermined depth and the polarized light is maintained in the polarized state at the predetermined depth. One or more detectors each including a detector polarizer coupled thereto are configured to discriminate the light maintained in the polarized state and at the predetermined depth and are configured to generate a plurality of frames of the tissue in the predetermined area at the predetermined depth. A controller is coupled to the one or more light sources and the one or more detectors. The controller is configured to: acquire the plurality of frames, select a region of interest having the same coordinates for each of the plurality of frames, average the number of pixels within each region of interest to create a raw reference signal, detrend the raw reference signal to create a detrended raw reference signal, perform frequency domain
(Continued)

analysis of the detrended raw reference signal, identify a frequency band of interest associated with the spontaneous hemodynamic oscillations, and perform an inverse fast Fourier transform within the frequency band of interest to generate a reference signal indicative of blood volume oscillations at a selected spontaneous hemodynamic oscillation. For each sample of the reference signal at a predetermined point in time, the controller multiplies the sample by each pixel of a frame at the same predetermined point in time to generate a three-dimensional coordinate matrix including a plurality of correlation matrix frames at each predetermined point in time. The controller adds the plurality of correlation matrix frames at each predetermined point in time to generate a two-dimensional hemodynamic map indicative of the strength of the spontaneous hemodynamic oscillation to assess the viability of the tissue in the predetermined area.

17 Claims, 7 Drawing Sheets

(56) References Cited

U.S. PATENT DOCUMENTS

| | | |
|---|---|---|
| 2010/0210931 A1 | 8/2010 | Cuccia et al. |
| 2013/0237860 A1 | 9/2013 | Ince |

OTHER PUBLICATIONS

Pichette et al., "Intraoperative video-rate hemodynamic response assessment in human cortex using snapshot hyperspectral optical imaging", Neurophotonics, 3(4) (2016), ten (10) pages.

Ryan C., et al., "Objective Estimates of the Probability of Death from Burn Injuries", New England Journal of Medicine 1998:338:362-6.

Orgill D., "Excision and Skin Grafting of Thermal Burns", New England Journal of Medicine Feb. 26, 2009;360(9):893-901.

Jaskille AD et al., Critical Review of Burn Depth Assessment Techniques: Part . Historical Review, Journal of Burn Care & Research, Nov./Dec. 2009, 937-947.

O'Reilly TJ et al., "Laser Doppler Flowmetry Evaluation of Burn Wound Depth", Journal of Burn Care Rehabilitation, 1989; 10:1-6.

Atiles L. et al., "Laser Doppler Flowmetry in Burn Wounds", Journal of Burn Care Rehabilitation, 1995, 16:388-393.

Benya R. et al., "Adverse Reactions of Indocyanine Green: A Case Report and a Review of the Literature; Catheterization and Cardiovascular Diagnosis", 1989 17(4):231-233.

Pierro ML et al., "Validation of a Novel Hermodynamic Model for Coherent Hemodynamics Spectroscopy (CHS) and Functional Brain Studies With fNIRS and fMRI", NeuroImage, vol. 85, Part 1, Jan. 15, 2014, (twenty-nine (29) pages).

Nitzan M. et al., "Spontaneous Low-Frequency Fluctuations in Finger Blood Volume, Measured by Photoplethysmography", Proceedings of SPIE, Event: BIOS Europe '95, 1995, Barcelona, Spain, vol. 2631, pp. 84-91.

Nitzan M. et al., "Measurement of the Variability of the Skin Blood Volume Using Dynamic Spectroscopy", Applied Surface Science 106 (1996):478-482.

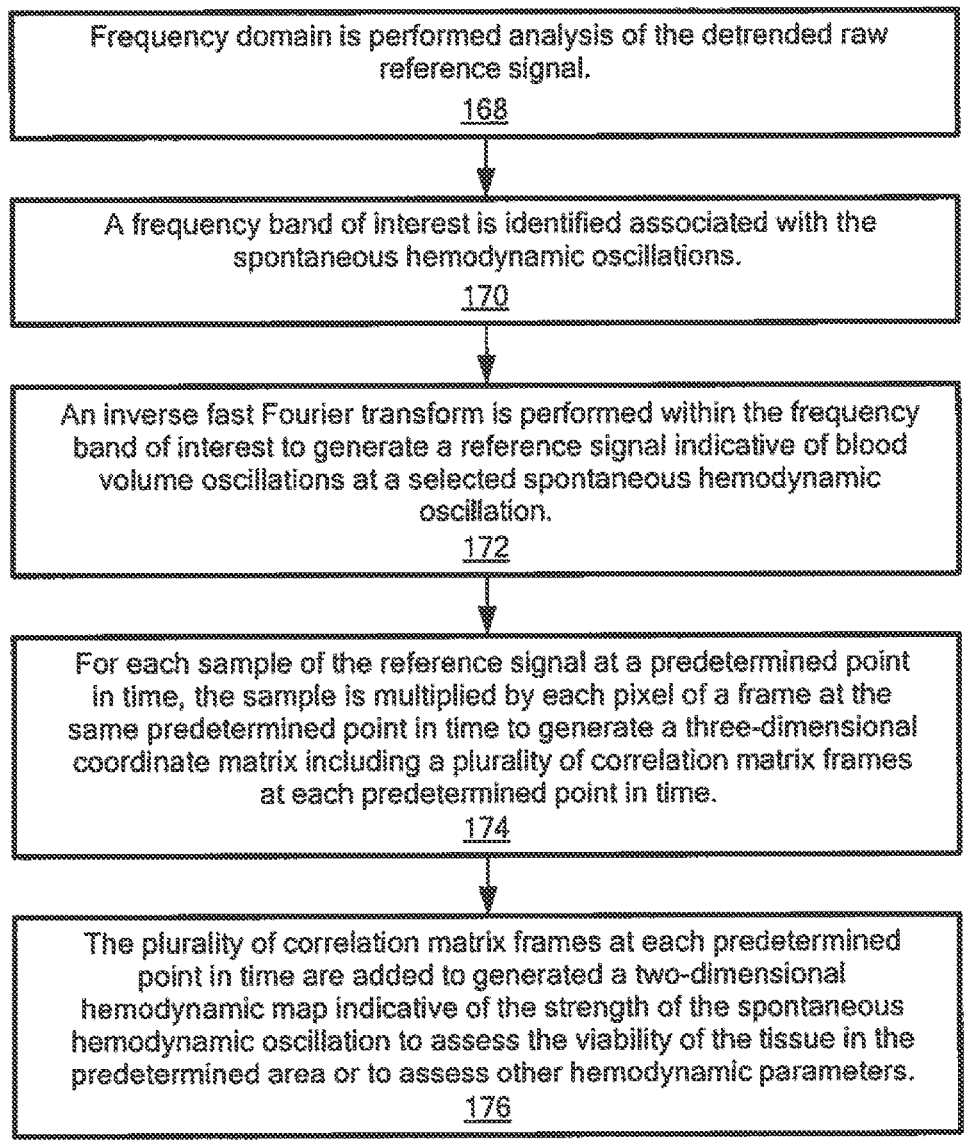
FIG. 6 (con't.)

CONTACTLESS SYSTEM AND METHOD FOR ASSESSING TISSUE VIABILITY AND OTHER HEMODYNAMIC PARAMETERS

RELATED APPLICATIONS

This application claims benefit of and priority to U.S. Provisional Application Ser. No. 62/621,873 filed Jan. 25, 2018, under 35 U.S.C. §§ 119, 120, 363, 365, and 37 C.F.R. § 1.55 and § 1.78, which is incorporated herein by this reference.

GOVERNMENT RIGHTS

This invention was made with government support under contract number W81XWH-17-C-0169, awarded by the Department of Defense. The government has certain rights in the invention.

FIELD OF THE INVENTION

This invention relates to a contactless system and method for assessing tissue viability and other hemodynamic parameters.

BACKGROUND OF THE INVENTION

Burn wounds may be classified into four categories of increasing depth: superficial, intermediate partial thickness, deep partial thickness, and full thickness. The latter two classifications typically require aggressive interventions that involve the debridement of necrotic tissue and the application of split thickness skin grafts. These are more morbid wounds typically wrought with the potential for hypertrophic scarring and contractures and may necessitate early surgical excision and grafting to optimize the outcome, See e.g., Ryan et al., *Objective Estimates of the Probability of Death From Burn Injuries*, N. Engl. J. Med., 1998, 338: 362-6, incorporated by reference herein. Selecting the level of debridement sufficient to minimize inflammation and determining the optimal treatment in a timely fashion is critical given the risks of infection and sepsis. The success of grafting depends on the removal of virtually all necrotic tissue and any biofilm and requires the presence of highly-vascularized granulation tissue. The goal of early debridement for grafting is to remove all the devitalized tissue for skin grafting until only granulation tissue remains. Using a conventional tissue excision procedure, several layers of burned tissue are excised until the viable wound bed is reached, as evidenced by capillary bleeding. See e.g., Orgill et al., *Excision and Skin Grating Of Thermal Burns*, New England Journal of Medicine, 2009, Feb. 26; 360(9): 893-901, incorporated by reference herein. Although bleeding is typically assumed to mean the tissue is viable, this conventional tissue excision procedure is subjective and imprecise because it relies on visual inspection that does not preclude the possibility that some necrotic tissue or biofilm will be inadvertently left in the wound site.

Given the challenges in objectively determining tissue viability, a number of conventional technologies have been repurposed with the intent of providing metrics of tissue viability, such as Laser Doppler Imaging (LDI) and Indocyanine green angiography (ICG).

Conventional LDI is a highly recognized noninvasive technique for clinical evaluation of burn wound and tissue viability assessment. Several conventional LDI devices are available which estimate the blood flow in the area of interest. See e.g., Jaskille et al., *Critical Review of Burn Depth Assessment Techniques: Part II, Review of Laser Doppler Technology*, Journal of Burn Care & Research, 2010, Jan. 1; 31(1):151-7, incorporated by reference herein. However, LDI has several drawbacks. Because flowmetry requires the probe to directly contact with the burn wound, it may increase the risk of wound infection and may inflict trauma to already vulnerable tissue. See e.g., O'Reilly et al., *Laser Doppler Flowmetry Evaluation of Burn Wound Depth*, Journal of Burn Care & Research, 1989, Jan. 1; 10(1):1, incorporated by reference herein. Additionally, because LDI measures perfusion in one spot at the time, assessing a large burn wound may be a time-consuming process. Additionally, there is some risk that LDI may not detect necrotic tissue in the wound bed. See e.g., Atiles et al., *Laser Doppler Flowmetry In Burn Wounds*, Journal of Burn Care & Research, 1995, Jul. 1; 16(4): 388-93, incorporated by reference herein.

Conventional Indocyanine green (ICG) video-angiography provides greater skin imaging penetration compared to LDI. ICG enables visualization of the deep dermal vasculature using a dye. See e.g., Jerath et al., *Burn Wound Assessment in Porcine Skin Using Indocyanine Green Fluorescence*, Journal of Trauma and Acute Care Surgery, 1999, Jun. 1; 46(6): 1085-8, incorporated by reference herein. ICG is based on the fluorescent properties of the dye being used and quantifying the intensity of the dye. ICG provides color-coded maps relative to the perfusion of the investigated area. The major drawback associated with conventional ICG video-angiography is that intravascular dye injection is required. Previous studies have shown a high degree of association between headache, pruritus, urticarial and anaphylactic reaction following the dye injection. See e.g., Benya et al., *Adverse Reactions to Indocyanine Green: A Case Report and a Review of the Literature*. Catheterization and Cardiovascular Diagnosis, 1989, Aug. 1; 17(4):231-3, incorporated by reference herein.

While conventional LDI and ICG each offer a unique approach to detecting tissue viability, both techniques are cumbersome to manipulate in a surgical setting, have a large size, and do not provide for real-time diagnosis, critical for tissue viability assessment during an excision procedure.

SUMMARY OF THE INVENTION

In one aspect, a contactless system for assessing tissue viability and other hemodynamic parameters is featured. The system includes one or more light sources configured to emit lights at a predetermined wavelength sensitive to hemoglobin concentration associated with spontaneous hemodynamic oscillations at tissue in a predetermined area of a human subject. One or more polarizers each coupled to one or more of the one or more light sources are configured to polarize the light to a polarized state such that the polarized light in the polarized state diffuses into the tissue in the predetermined area at a predetermined depth and the polarized light is maintained in the polarized state at the predetermined depth. One or more detectors each including a detector polarizer coupled thereto are configured to discriminate the light maintained in the polarized state and at the predetermined depth and configured to generate a plurality of frames of the tissue in the predetermined area at the predetermined depth. A controller is coupled to the one or more light sources and the one or more detectors and is configured to: acquire the plurality of frames, select a region of interest having the same coordinates for each of the plurality of frames, average the number of pixels within each region of interest to create a raw reference signal, detrend the raw reference signal to create a detrended raw reference signal, perform frequency domain analysis of the detrended raw reference signal, identify a frequency band of interest associated with the spontaneous hemodynamic oscillations, perform an inverse fast Fourier transform within the frequency band of interest to generate a reference signal indicative of blood volume oscillations at a selected spontaneous hemodynamic oscillation, for each sample of the reference signal at a predetermined point in time, multiply the sample by each pixel of a frame at the same predetermined point in time to generate a three-dimensional coordinate matrix including a plurality of correlation matrix frames at each predetermined point in time, and add the plurality of correlation matrix frames at each predetermined point in time to generate a two-dimensional hemodynamic map indicative of the strength of the spontaneous hemodynamic oscillation to assess the viability of the tissue in the predetermined area.

In one embodiment, the spontaneous hemodynamic oscillations may have a frequency in the range of 0.05 Hz to about 1.5 Hz. The predetermined wavelength may be in the range of about 500 nm to about 1,000 nm. The predetermined depth may be in the range of about 0.1 mm to about 0.5 mm. The other hemodynamic parameters may include one or more of: heart rate, resting heart rate, heart rate variability, and tissue saturation for patients suffering from diminished blood circulation, and other similar type hemodynamic parameters. The one or more detectors may include a CCD camera. The one or more detectors may include a CMOS camera. The predetermined area may include a burn area of the human subject. The predetermined area may include a wound area of a human subject. The system may include a light filtering lens coupled to one or more light sources.

In another aspect, a contactless method for assessing tissue viability and other hemodynamic parameters is featured. The method includes emitting light at a predetermined wavelength sensitive to hemoglobin concentration associated with spontaneous hemodynamic oscillations at tissue in a predetermined area of a human subject. The light is polarized to a polarized state such that the polarized light in the polarized state diffuses into the tissue in the predetermined area at a predetermined depth and the polarized light is maintained in the polarized state at the polarized depth. The light maintained in the polarized state and at the predetermined depth is discriminated. A plurality of frames of the tissue in the predetermined area at the predetermined depth are generated and acquired. A region of interest is selected having the same coordinates for each of the plurality of frames. The number of pixels within each region of interest is averaged to create a raw reference signal. The raw reference signal is detrended to create a detrended raw reference signal. A frequency domain analysis of the detrended raw reference signal is performed. A frequency band of interest associated with the spontaneous hemodynamic oscillations is identified. An inverse fast Fourier transform within the frequency band of interest is performed to generate a reference signal indicative of blood volume oscillations at a selected spontaneous hemodynamic oscillation. For each sample of the reference signal at a predetermined point in time, the sample is multiplied by each pixel of a frame at the same predetermined point in time to generate a three-dimensional coordinate matrix including a plurality of correlation matrix frames at each predetermined point in time. The plurality of correlation matrix frames at each predetermined point in time are added to generate a two-dimensional hemodynamic map indicative of the strength of the spontaneous hemodynamic oscillation to assess the viability of the tissue in the predetermined area.

In one embodiment, the plurality of correlation matrix frames at each predetermined point in time are added to generate a two-dimensional hemodynamic map indicative of the strength of the spontaneous hemodynamic oscillation to assess the viability of other hemodynamic parameters including one or more of: heart rate, resting heart rate, heart rate variability, and tissue saturation for patients suffering from diminished blood circulation and similar type hemodynamic parameters. The spontaneous hemodynamic oscillations may have a frequency in the range of 0.05 Hz to about 1.5 Hz. The predetermined wavelength may be in the range of about 500 nm to about 1,000 nm. The predetermined depth may be in the range of about 0.1 mm to about 0.5 mm. The predetermined area may include a burn area of the human subject. The predetermined area may include a wound area of a human subject.

The subject invention, however, in other embodiments, need not achieve all these objectives and the claims hereof should not be limited to structures or methods capable of achieving these objectives.

BRIEF DESCRIPTION OF THE SEVERAL VIEWS OF THE DRAWINGS

Other objects, features and advantages will occur to those skilled in the art from the following description of a preferred embodiment and the accompanying drawings, in which.

DETAILED DESCRIPTION OF THE INVENTION

Figure 1:
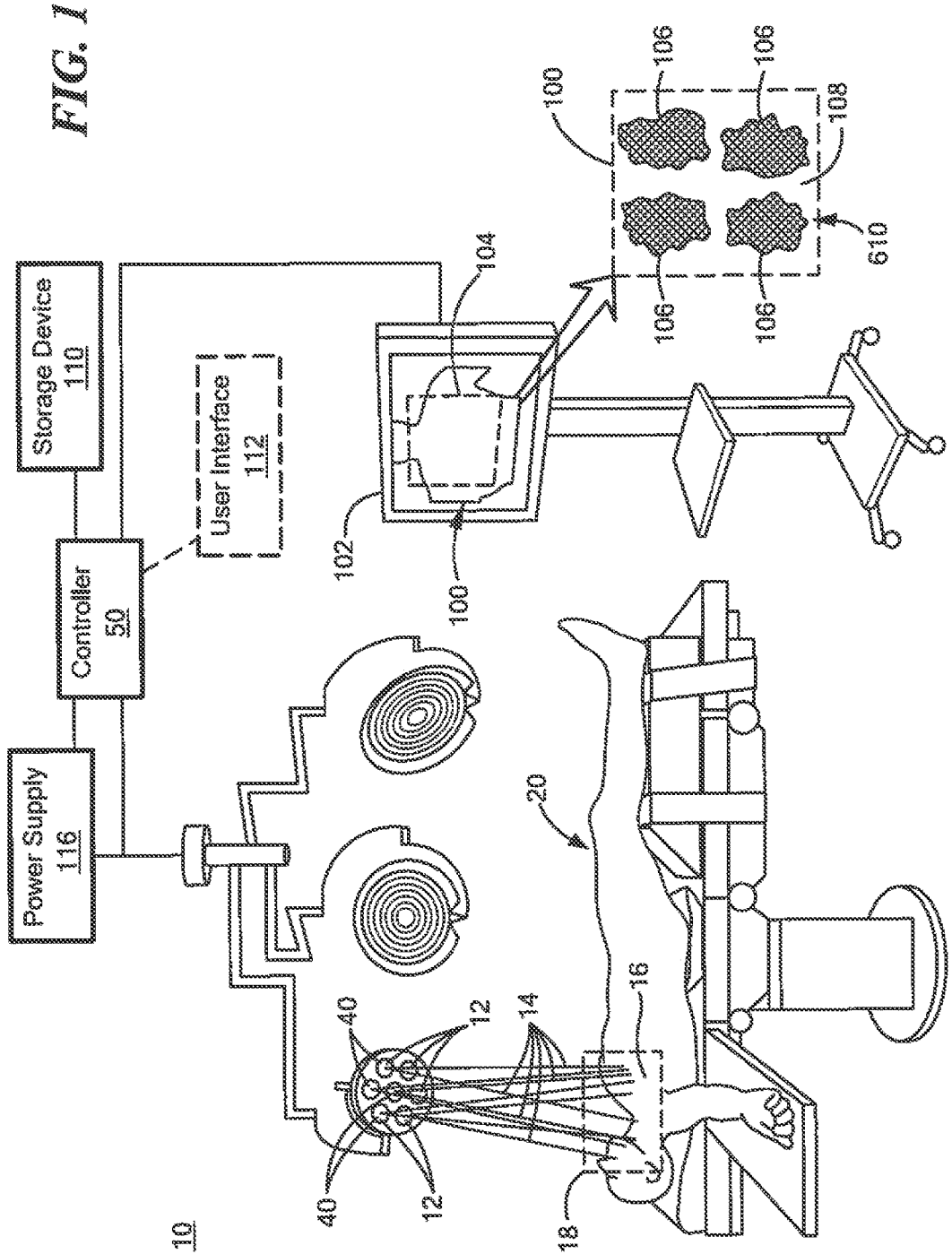
FIG. 1 is a schematic diagram showing the primary components of one embodiment of the contactless system and method for assessing tissue viability and other hemodynamic parameters.

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings. If only one embodiment is described herein, the claims hereof are not to be limited to that embodiment. Moreover, the claims hereof are not to be read restrictively unless there is clear and convincing evidence manifesting a certain exclusion, restriction, or disclaimer.

FIG. 1 shows one embodiment of contactless system 10 for assessing of tissue viability and other hemodynamic parameters. System 10 preferably includes one or more light sources 12 configured to emit light 14 at a predetermined wavelength sensitive to hemoglobin concentration associated with spontaneous hemodynamic oscillations at tissue 16 in predetermined area 18 of a human subject 20 having a burn wound or similar type wound where the tissue viability of human subject 20 needs to be determined, as discussed in the Background section above. Tissue 16 in predetermined area 18 may be any tissue in any area on human subject 20 having a burn wound or similar type wound, e.g., such as diabetic ulcers or similar type wounds. In the example shown in FIG. 1, predetermined area 18 is located on the face, neck, and upper chest of human subject 20. In other examples, predetermined area 18 may be any area of the human subject 20 having a burn wound or similar type wound where tissue viability needs to be determined. One or more light sources 12 are preferably placed above and proximate tissue 16 in predetermined area 18 and emit or illuminate light 14 having one or more wavelengths sensitive to hemoglobin concentration spontaneous oscillations and capable of probing the human tissue without being completely absorbed, as discussed in further detail below. In one example, one or more light sources 12 preferably emit or illuminate light 14 having wavelengths in an electromagnetic (EM) spectrum, e.g., in the range of about 500 nm to about 1000 nm. In one example, the spontaneous hemodynamic oscillations, e.g., cardiac and respiratory induced oscillations, have a frequency in the range of about 0.05 Hz to about 1.5 Hz associated with blood volume changes. In one design, one or more light sources 12 may include near infrared (NIR) sensors and/or one or more near infrared spectroscopy (NIRS) sensors.

Figure 2:
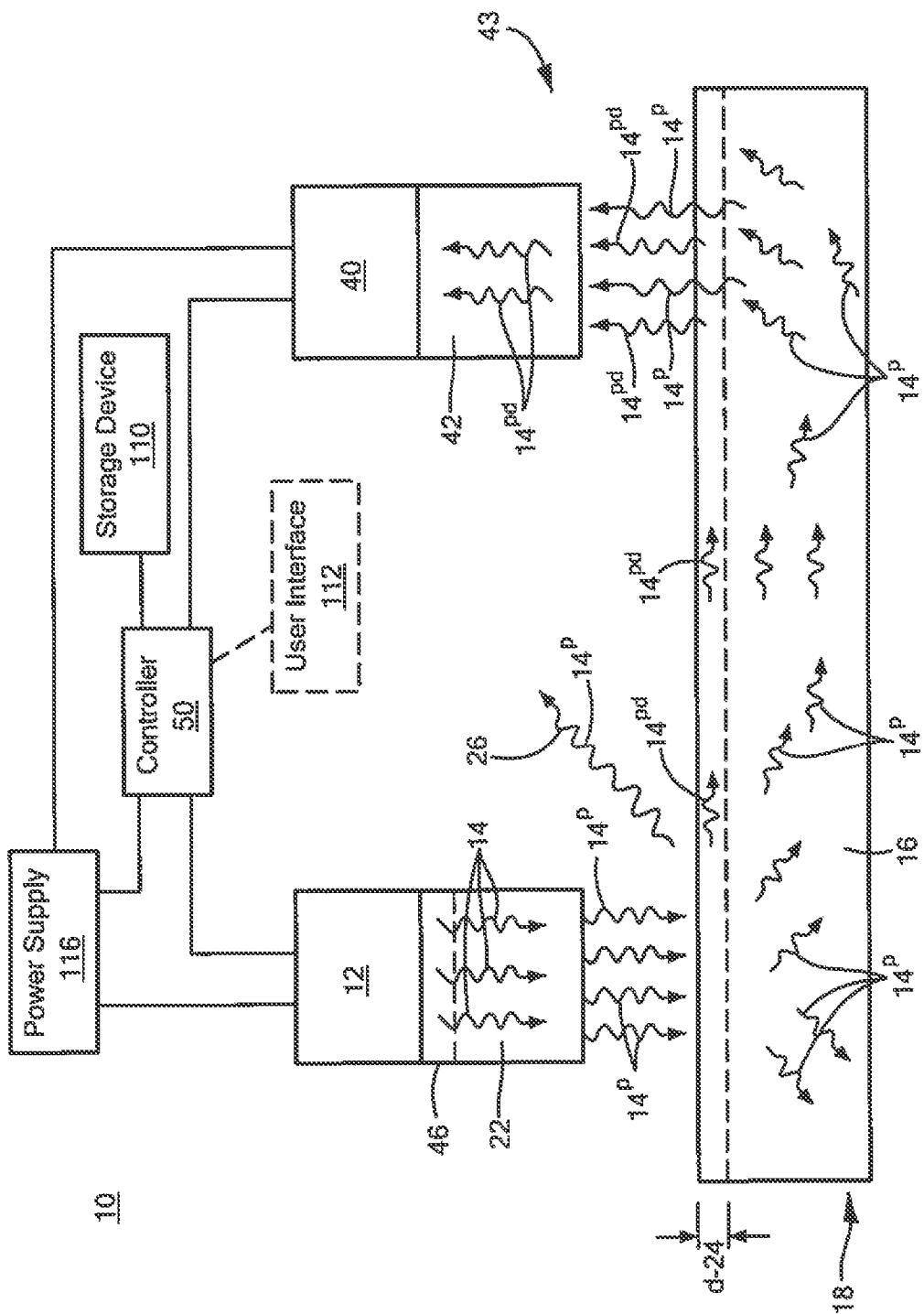
FIG. 2 is a schematic diagram showing in further detail the interaction of polarized light in a polarized state with tissue in the predetermined area shown in FIG. 1.

System 10 also includes one or more polarizers each coupled to one or more light sources. FIG. 2 shows an example of polarizer 22 coupled to light source 12. Each of the one or more light sources 12 shown in FIG. 1 similarly has polarizer 22 coupled thereto. Each polarizer 22, FIG. 2, coupled to light source 12 is configured to polarize light 14 to polarized light $14^P$ in a polarized state such that polarized light $14^P$ in the polarized state diffuses into tissue 16 in predetermined area 18 and polarized light $14^P$ is maintained in the polarized state at predetermined depth d-24. In one example, depth d-24 is in the range of about 0.1 mm to about 0.5 mm. For example, when polarized light $14^P$ is incident on tissue 16 in predetermined area 18, some of the photons polarized light $14^P$ will reflect off the surface of tissue 16 and some photons will penetrate into tissue 16 where the photons will either be scattered or absorbed as shown. If light polarized $14^P$ incident light is reflected off the surface of the tissue 16, e.g., indicated at 26, the polarization state is perfectly maintained. However, the polarization state of the penetrating photons of polarized light $14^P$ may be affected by scattering events in tissue 16 which may be divided into two categories: polarization maintaining or depolarized. If the photons do not travel deep into the tissue of tissue 16 only a limited number of scattering events will occur and the polarization is maintained, but some alterations have likely occurred. However, if photons travel deeper into tissue 16 and more scattering events occur, the polarization of polarized light $14^P$ becomes increasingly depolarized. Therefore, by utilizing one or more polarizer 22 each coupled to one or more light sources 12, the degree of polarization can be maintained to discriminate the depth of penetration of light into the tissue of tissue 16, e.g., polarized light $14^{pd}$ at depth d-24, e.g., is about 0.1 mm to about 0.5 mm. Such a depth is typically needed for real-time assessment of tissue viability of tissue 16 in predetermined area 18 by clinicians in an objective manner, as discussed below.

Polarized light $14^P$ emitted from each polarizer 22 provides a relatively low-cost solution to enable real-time assessment of the tissue viability and other hemodynamic parameters of tissue 16 in predetermined area 18. As polarized light $14^P$ transversely propagates through time and space, it contains both oscillating orthogonal electric and magnetic field vectors. The polarization of polarized light $14^P$ as disclosed herein refers to the direction and manipulation of the oscillating electric field vector. Polarization may be produced and manipulated by polarizer 22 coupled to one or more light sources 12. Polarizer 22 may be placed in any desired position along path of light 14 from detectors 12, FIGS. 1 and 2, to tissue 16 in predetermined area 18. Polarized light 14 provided by one or more light sources 12 and polarizer 22 coupled thereto may include linearly polarized light 14', FIG. 3, circular polarized 14" or elliptical polarized light 14''', depending on the arrangement of the optical components used. Linearly polarized light 14' may be produced when a single electric field oscillation plane is isolated using polarizer 22 configured as linear polarizer, where one oscillation plane is dictated by the polarizing axis. The resulting electric field vector is considered to oscillate in one plane in which the orthogonal Ex-30 and Ey-32 components are maintained the same phase and amplitude as shown. Circularly polarized light 14" may be provided by polarizer 22 coupled to one or more light sources 12 when one of the two Ex-30 and Ey-32 components of the linearly polarized electric field vector becoming out of phase by exactly ±90 from the other as shown. Circularly polarized light 14" may be provided by polarizer 22 coupled to one or more light sources 12 when polarizer 22 is configured as a quarter-wave plate rotated 45 degrees relative to the polarizing axis of the linear polarizer. As circularly polarized light propagates through time, the shape of the propagation may be considered as a helix rotating either clockwise or counter-clockwise, which is denoted as right-handed or left-handed respectively. Elliptically polarized light 14''' is provided by polarizer 22 coupled to one or more light sources 12 when linearly polarized light passing through polarizer 22 is configured as a wave plate or birefringent material where the electric field vector components become out of phase by any amount other than ±90 degrees. Polarized light 14', polarized light 14" or polarized light 14''' provided by polarizer 36 coupled to one or more light sources 12 under these different polarization states will respond differently when focused on a turbid media, such as tissue 16, FIG. 1, of human subject 20 in predetermined area 18.

Figure 3:
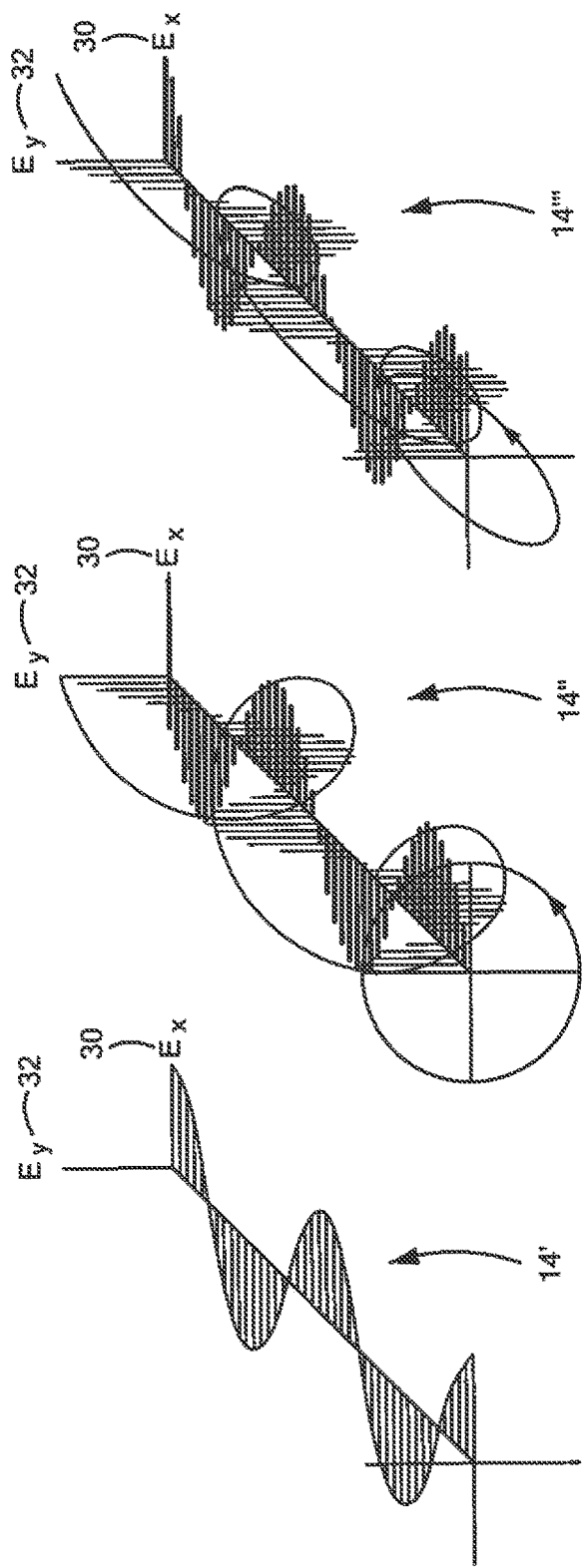
FIG. 3 depicts graphs of various types of polarized light which may be provided by the polarizer coupled to the one or more light sources shown in FIG. 1.

In the example discussed above with reference to FIG. 2, polarized light $14^P$ and polarized light $14^{pd}$ may be one or more of polarized light 14', 14", and/or 14''', FIG. 3.

System 10 may also include one or more light filtering lenses coupled to one or more light sources 12, e.g., light filtering lens 46 shown coupled to polarizer 22. Light filtering lens 46 is preferably configured to be transmissive within the desired operating spectrum discussed above and configured to block EM waves outside of the desired spectrum.

System 10 also includes one or more detectors 40, FIGS. 1 and 2, which each include detector polarizer 42, FIG. 2, coupled thereto. In one example, one or more detectors 40 preferably include one or more high-quality CCD cameras, one or more CMOS cameras, or similar type detectors. One or more detectors 40 may each include sensors having an analog amplifier and filter configured to increase the gain on the signal and reduces background noise to create clean images.

Each of detector polarizer 42 are configured to discriminate between polarized light $14^{pd}$ maintained in the polarized state and at the predetermined depth, d-24, in from tissue 16 and polarized light $14^p$ reflected from tissue 16 which has not been maintained in the polarized state and at the predetermined depth. For example, as shown generally by arrow 43, each detector polarizer 42 coupled to detector 40 discriminates between polarized light $14^{pd}$ that has been maintained in the polarized state at predetermined depth, d-24, in tissue 16 and polarized light $14^p$ which has not been maintained in the polarized state at predetermined depth, d-24.

Figure 4:
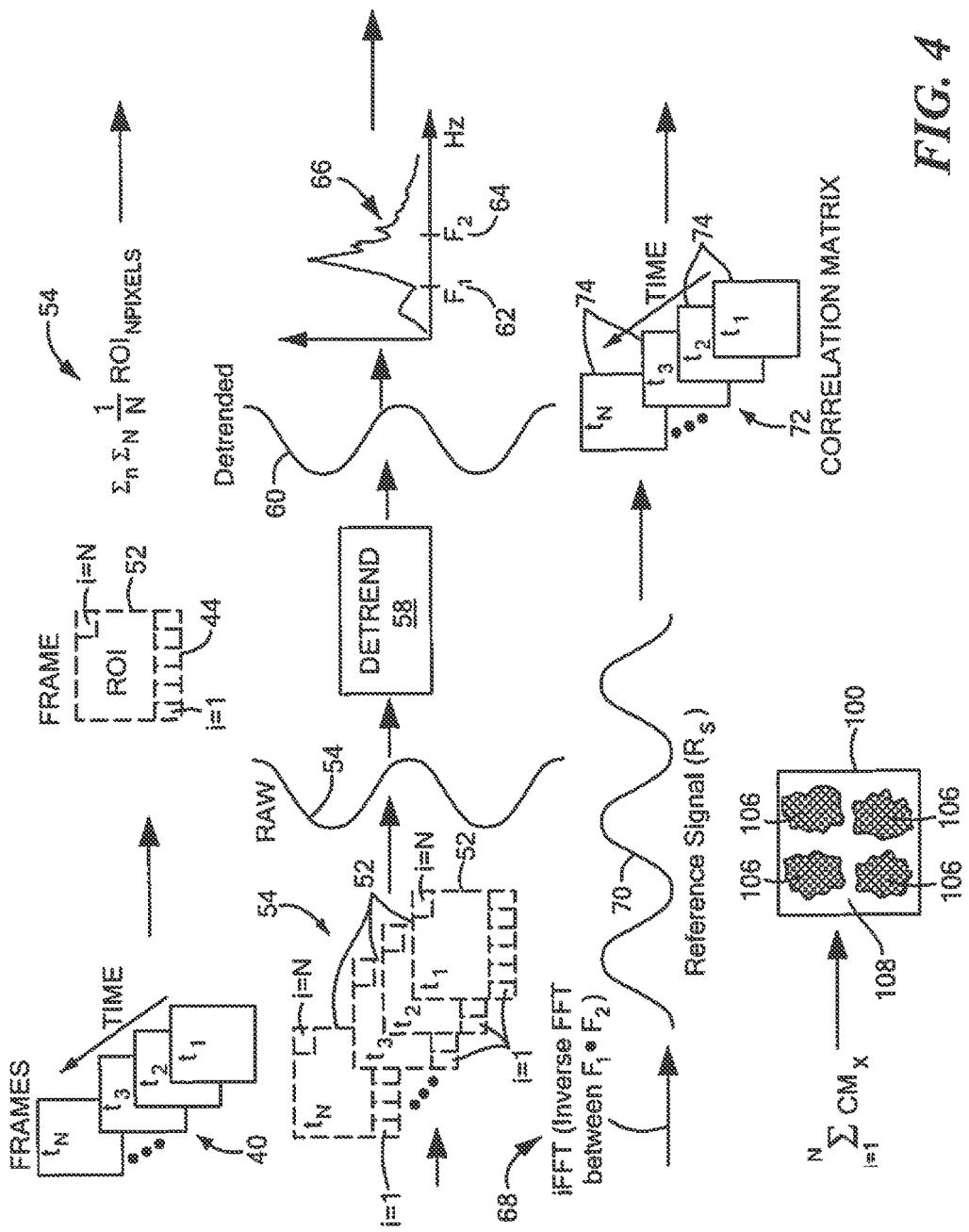
FIG. 4 is a block diagram showing one example of the primary steps performed by the controller shown in FIG. 1 to create a hemodynamic map to assess tissue viability and other hemodynamic parameters.

One or more detectors 40, FIGS. 1 and 2, e.g., one or more CCD cameras or CMOS cameras, or similar type devices, are configured to generate a plurality of frames of tissue 16, FIGS. 1 and 2, in predetermined area 18 from discriminated polarized light $14^{pd}$ reflected from tissue 16 in predetermined area 18 at predetermined depth, d-24, FIG. 2, e.g., plurality of frames 40, FIG. 4, at different points in time ranging from, $t_1, t_2, t_3 \ldots t_N$.

System 10 also includes controller 50, FIGS. 1 and 2, coupled to one or more light sources 12 and one or more detectors 40. Controller 50 may be a processor, one or more processors, an application-specific integrated circuit (ASIC), firmware, hardware, and/or software (including firmware, resident software, micro-code, and the like) or a combination of both hardware and software that may all generally be referred to herein as a "controller", which may be part of contactless system 10 and method thereof for assessing tissue viability and other hemodynamic parameters. Computer program code for the programs for carrying out the instructions or operation of controller 50 may be written in any combination of one or more programming languages, including an object oriented programming language, e.g., C++, Smalltalk, Java, and the like, or conventional procedural programming languages, such as the "C" programming language or similar programming languages.

Controller 50 acquires the plurality of frames 40, FIG. 4, to provide image acquisition, preferably at a high rate, e.g., greater than about 5 frames per second (fps). Controller 50 then selects a region of interest (ROI) having the same coordinate for each of the plurality of frames. For example, ROI-52, which includes pixels from i=1 to i=N as shown, is selected by controller 50 from frame 44 at point $t_1$. Similarly, controller 50 selects a ROI-52 having the same pixel coordinates for each of the plurality of frame 44 at points of time, $t_1, t_2, t_3 \ldots t_N$.

Controller 50 then averages the number of pixels from i=I to i=n within each ROI-52 of each of the plurality of frames 40, at times $t_1, t_2, t_3 \ldots t_N$, indicated at 54, to create raw reference signal 56. In one example, controller 50 uses equation (1) below to averages the number of pixels within each ROI-52:

$$\sum_N \sum \frac{1}{n} ROI_{NPIXELS} \quad (1)$$

where n is the number of pixels in the selected ROI and N is the number of acquired frames.

Controller 50 then detrends raw reference signal 56, indicated at 58, to create detrended raw reference signal 60.

Controller 50 then performs frequency domain analysis of detrended raw reference signal 60 and identifies a frequency band of interest associated with the spontaneous hemodynamic oscillations. In this example, controller 50 has identified the frequency band of interest between $F_1$-62 and $F_2$-64 associated with spontaneous hemodynamic oscillations 66. The frequency band of interest associated with the spontaneous hemodynamic oscillations is typically in the range of 0.05 Hz to about 1.0 Hz, as discussed above.

Controller 50 then performs inverse fast Fourier transform (iFFT), indicated at 68, within the frequency band of interest, $F_1$-62 to $F_2$-64, to generate reference signal ($R_s$) 70 indicative of blood volume oscillations at selected hemodynamic oscillations.

Figure 5:
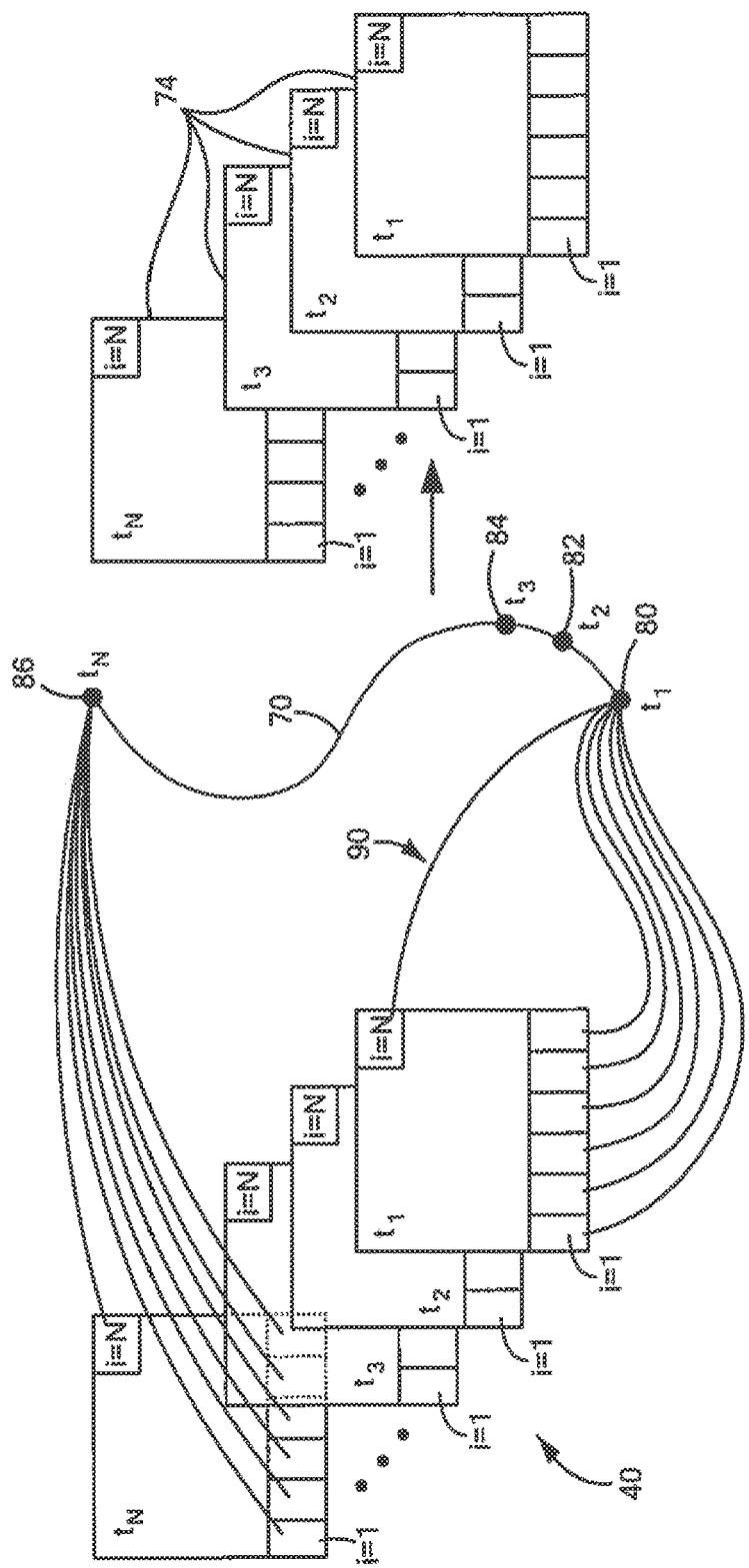
FIG. 5 is a schematic block diagram showing in further detail one example of the step of creating the hemodynamic map shown in FIG. 4.

For each sample of reference signal 70 at a predetermined point in time, controller 50 multiplies the sample by each pixel of a frame at the same predetermined point in time to generate three-dimensional correlation matrix 72 which includes a plurality of correlation matrix frames 74 at each predetermined point in time. As discussed above, each of the plurality of frames 40 is acquired at a various point of time, e.g., time ranging from $t_1, t_2, t_3, \ldots t_N$. Reference signal 70, shown in greater detail in FIG. 5, includes the same number of samples as the number of plurality of frames 40, FIG. 4, e.g., sample-80, FIG. 5, at time $t_1$, sample 82 at time $t_2$, sample 84 at time $t_3$ and sample 86 at time $t_N$. Controller 50 multiplies each sample by each pixel of each of the plurality of frames 40 to generate correlation matrix 72 with a plurality of correlation matrix frames 74. In this example, sample 80 at time $t_1$ is shown being multiplied each of the pixels ranging from i=1 to i=n of frame 44 at the same time $t_1$, as indicated by lines 90. Similarly, sample 88 at time $t_N$ is shown being multiplied each of the pixels ranging from i=1 to i=n of frame 44 at the same time $t_N$. The same is done for all of the samples at each point in time.

In one example, correlation matrix 72 is generated using equation (2):

$$FRAME_i * R_{Si} \quad (2)$$

where $FRAME_i$ is each individual pixels in specific frame at time i, e.g., $t_1, t_2, t_3, \ldots t_N$, and $R_{Si}$ is a sample at time i of the Reference Signal, e.g., $t_1, t_2, t_3, \ldots t_N$.

Controller 50 then adds the plurality of correlation matrix frames 74 at each predetermined point in time to generate two-dimensional hemodynamic map 100, FIG. 4, indicative of the strength of spontaneous hemodynamic oscillations to assess the viability of tissue 16 in predetermined area 18. In one example, equation (3) below is used to generate two-dimensional hemodynamic map 100:

$$\sum_{i=1}^{N} CMx \quad (3)$$

where i is correlation matrix at time, i, e.g., $t_1, t_2, t_3, \ldots t_N$. N is the total amount of is acquired frames, and CMx is the hemodynamic map showing areas of viable tissue.

In one design, system 10, FIG. 1, preferably includes display device 102 coupled electronically or wirelessly to controller 50, e.g., a computer monitor, a smart phone, a tablet, or similarly type device, which displays two-dimensional hemodynamic map 100.

The result is system 10 provides hemodynamic map 100, FIGS. 1 and 2, of tissue 16 in predetermined area 18 and at a depth of about 0.1 mm to about 0.5 mm needed for real-time assessment of the viability of tissue 16 in predetermined area 18 or other hemodynamic parameters, e.g., heart rate, resting heart rate, heart rate variability, tissue saturation for patients suffering from diminished blood circulation, and the like. In one design, system 10 provides hemodynamic map 100 which shows viable and necrotic tissue areas. If hemodynamic oscillations are detected and shown on hemodynamic map 100, e.g. indicated at 106 in caption 108, or shown in FIG. 4, the tissue is viable. If hemodynamic oscillations are not shown, and therefore not detected by the procedure described above, on hemodynamic map 100, the tissue is necrotic, e.g., indicated at 108, FIGS. 1 and 4.

Hemodynamic map 100, FIGS. 2 and 4, preferably has a maximum field of view (FOV) of tissue 16 in predetermined area 18 where tissue viability needs to be determined. In one design, the FOV, e.g., FOV-104, FIG. 1, displayed on display device 102 provides a real-time view of tissue 16 in predetermined area 18 needed for real-time assessment of tissue viability in an objective manner. In one example, FOV-104 of tissue 16 in predetermined area 18 may be about 10 inches by 10 inches. In other examples, FOV-104 of tissue 16 in predetermined area 18 may be larger or smaller than 10 inches by 10 inches as needed.

Controller 50, FIGS. 1 and 2, is also preferably configured to store data associated with one or more hemodynamic maps 100 created by controller 100 in storage device 110. Storage device 110 may include any combination of computer-readable media or memory. The computer-readable media or memory may be a computer-readable signal medium or a computer-readable storage medium. A computer-readable storage medium or memory may be, an electronic, magnetic, optical, electromagnetic, infrared, or semiconductor system, apparatus, or device, or any suitable combination of the foregoing. Other examples may include an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. As disclosed herein, the computer-readable storage medium or memory may be any tangible medium that can contain, or store one or more programs for use by or in connection with one or more processors on a computing device such as a computer, a tablet, a cell phone, a smart device, or similar type device. Controller 50 may also be configured to compress the data associated with the hemodynamic maps.

To reduce and minimize the impact of uncontrolled ambient light changes, system 10 and the method thereof may implement spectral estimation techniques of the ambient illumination to remove uncontrolled ambient light changes. In other designs, system 10 and the method thereof may remove ambient lighting artifacts at the acquisition level by removing temporal changes in ambient illumination measured during programmed periods of non-active tissue illumination.

System 10 also preferably includes user interface 112 coupled to controller 50 electronically or wirelessly which may allow a user of system 10 to visualize and interact with the stored or real-time data. Data may be retrieved from controller 50 and storage device 110 via a data jack or by wireless communication, as known by those skilled in the art. System 10 also includes power supply 116 configured to provide power to one or more light sources 12, one or more detectors 20, controller 50, and/or display device 102. In one design, power supply 116 may include batteries for portable applications.

In other designs, contactless system 10 and method for assessing tissue viability and other hemodynamic parameters may be a standalone device for operation room, a portable device, or integrated into wearable tools wore by medical personnel.

Figure 6:
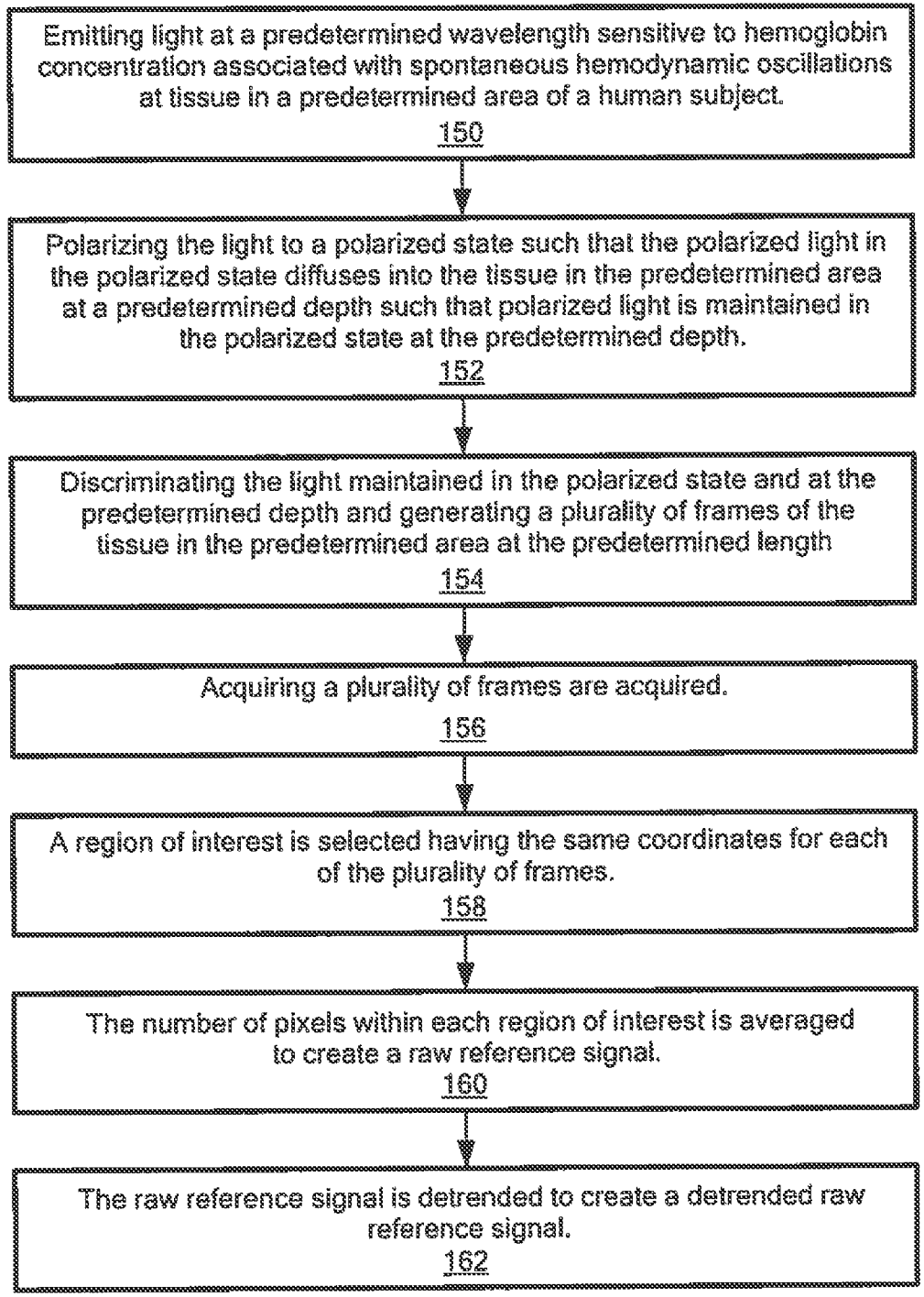
FIG. 6 is a schematic block diagram showing one example of the primary steps of one embodiment of the contactless method for assessing tissue viability and other hemodynamic parameters.

One example of the method for assessing tissue viability and other hemodynamic parameters includes emitting light at a predetermined wavelength sensitive to hemoglobin concentration associated with spontaneous hemodynamic oscillations at tissue in a predetermined area of a human subject, step 150, FIG. 6. The method also includes polarizing the light to a polarized state such that the polarized light in the polarized state diffuses into the tissue in the predetermined area at a predetermined depth such that the polarized light is maintained in the polarized state at the polarized depth, step 152. The method also includes discriminating the light maintained in the polarized state and at the predetermined depth and generating a plurality of frames of the tissue in the predetermined area at the predetermined depth, step 154. A plurality of frames are then acquired, step 156. A region of interest is then selected having the same coordinates for each of the plurality of frames, step 158. The number of pixels within each region of interest is averaged to create a raw reference signal, step 160. The raw reference signal is detrended to create a detrended raw reference signal, step 162. Frequency domain analysis is performed of the detrended raw reference signal, step 168. A frequency band of interest is identified associated with the spontaneous hemodynamic oscillations, step 170. An inverse fast Fourier transform (iFFT) is performed within the frequency band of interest to generate a raw reference signal indicative of blood volume oscillations at a selected spontaneous hemodynamic oscillation, step 172. For each sample of the raw reference signal at a predetermined point in time, the sample is multiplied by each pixel of a frame at the same predetermined point in time to generate a three-dimensional coordinate matrix including a plurality of correlation matrix frames at each predetermined point in time, step 174. The plurality of correlation matrix frames at each predetermined point in time are added to generate a two-dimensional hemodynamic map indicative of the strength of the spontaneous hemodynamic oscillations to assess the viability of tissue in the predetermined area or assess the viability of other hemodynamic parameters, step 176.

The result is system 10 and the method thereof provides a contactless real-time assessment of tissue viability and other hemodynamic parameters that allows a user to quantitatively assess the tissue health to provide objective metrics to support and guide accurate tissue excision of a burn wound or similar type wound. System 10 and the method thereof allows clinicians to selecting a level of debridement of a burn wound at a desired depth to minimize inflammation and determine the optimal treatment and remove virtually all the necrotic tissue in the burn wound or similar type wound in a time efficient manner. System 10 and the method thereof eliminates the need for intrusive tissue contact and preferably provides for long distance tissue viability assessment monitoring when compared to more conventional invasive imaging systems and methods discussed in the Background section. System 10 and the method thereof may provide opportunities in settings where multi-individual assessment may be extremely difficult or not feasible, such as intensive care units, emergency rooms, or where the condition of the patient may not allow for contact measurements.

One advantage of system 10 and the method thereof relying on spontaneous hemodynamic oscillation measurements discussed above with reference to one or more of FIG.

1-6, rather than absolute concentration measurements of chromophores present in the cardiovascular system, is an optical path length factor approximation is not required by system 10 and the method thereof. This may eliminate the need to rely on estimation errors. System 10 and method thereof, unlike conventional near infrared spectroscopy (NIRS) techniques, preferably does not require absolute concentration retrieval of the chromophores present in the cardiovascular system of tissue 16 of predetermined area 18 of human subject 16. Instead, system 10 and the method thereof preferably utilizes controller 50, one or more light sources 12, and one or more detectors 20. In one example.

For enablement purposes only, the following code portions are provided which can be executed on one or more processor, a computing device, or computer to carry out the primary steps and/or functions of contactless system 10 and method for assessing tissue viability and other hemodynamic parameters discussed above with reference to one or more of FIGS. 1-6. Other equivalent algorithms and code can be designed by a software engineer and/or programmer skilled in the art using the information provided herein.

```
%Acquire image
Frame = get frame (n,m) from camera/sensors etc.
%Determine ROI (region of interest)
maskmother = zeros(n,m) %set to zero a matrix equal to the size of the acquired
image
% Set to 1 an area of interest where reference signal will be calculated from
mask_1 = ones (maskmother (n,m) )
%Average pixels within selected ROI:
im = Frame.* mask_1
%Detrend im signal
im = im – im_Trend
%identify frequency components in im signal by FFT (Fast Fourier Transform)
PSD = FFT (im)
%Extrapolate Reference Signal by performing Inverse Fourier Transform only
between frequency range of interest (for example HR, respiration rate etc.).
Discard imaginary part
Ref = Real [FFT$^{-1}$( PSD(C1<f<C2) )]
%Integrate reference signal and acquired images product over time to obtain
hemodynamic map (S):
S = sum$_t$ (Ref.*Frame)
```

Although specific features of the invention are shown in some drawings and not in others, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments.

In addition, any amendment presented during the prosecution of the patent application for this patent is not a disclaimer of any claim element presented in the application as filed: those skilled in the art cannot reasonably be expected to draft a claim that would literally encompass all possible equivalents, many equivalents will be unforeseeable at the time of the amendment and are beyond a fair interpretation of what is to be surrendered (if anything), the rationale underlying the amendment may bear no more than a tangential relation to many equivalents, and/or there are many other reasons the applicants cannot be expected to describe certain insubstantial substitutes for any claim element amended.

Other embodiments will occur to those skilled in the art and are within the following claims.

What is claimed is:

1. A contactless system for assessing tissue viability and other hemodynamic parameters, the system comprising:
   one or more light sources configured to emit lights at a predetermined wavelength sensitive to hemoglobin concentration associated with spontaneous hemodynamic oscillations at tissue in a predetermined area of a human subject;
   one or more polarizers each coupled to one or more of the one or more light sources configured to polarize the light to a polarized state such that the polarized light in the polarized state diffuses into the tissue in the predetermined area at a predetermined depth and the polarized light is maintained in the polarized state at the predetermined depth;
   one or more detectors each including a detector polarizer coupled thereto configured to discriminate the light maintained in the polarized state and at the predetermined depth and configured to generate a plurality of frames of the tissue in the predetermined area at the predetermined depth; and
   a controller coupled to the one or more light sources and the one or more detectors, the controller configured to:
   acquire the plurality of frames,
   select a region of interest having the same coordinates for each of the plurality of frames,
   average the number of pixels within each region of interest to create a raw reference signal,
   detrend the raw reference signal to create a detrended raw reference signal,
   perform frequency domain analysis of the detrended raw reference signal,
   identify a frequency band of interest associated with the spontaneous hemodynamic oscillations,
   perform an inverse fast Fourier transform within the frequency band of interest to generate a reference signal indicative of blood volume oscillations at a selected spontaneous hemodynamic oscillation,
   for each sample of the reference signal at a predetermined point in time, multiply the sample by each pixel of a frame at the same predetermined point in time to generate a three-dimensional coordinate matrix including a plurality of correlation matrix frames at each predetermined point in time, and
   add the plurality of correlation matrix frames at each predetermined point in time to generate a two-dimensional hemodynamic map indicative of the strength of the spontaneous hemodynamic oscillation to assess the viability of the tissue in the predetermined area.

2. The system of claim 1 in which the spontaneous hemodynamic oscillations have a frequency in the range of 0.05 Hz to about 1.5 Hz.

3. The system of claim 1 in which the predetermined wavelength is in the range of about 500 nm to about 1,000 nm.

4. The system of claim 1 in which the predetermined depth is in the range of about 0.1 mm to about 0.5 mm.

5. The system of claim 1 in which the other hemodynamic parameters include one or more of: heart rate, resting heart rate, heart rate variability, and tissue saturation for patients suffering from diminished blood circulation.

6. The system of claim 1 in which the one or more detectors include a CCD camera.

7. The system of claim 1 in which the one or more detectors include a CMOS camera.

8. The system of claim 1 in which the predetermined area includes a burn area of the human subject.

9. The system of claim 1 in which the predetermined area includes a wound area of a human subject.

10. The system of claim 1 further including a light filtering lens coupled to one or more light sources.

11. A contactless method for assessing tissue viability and other hemodynamic parameters, the method comprising:
    emitting light at a predetermined wavelength sensitive to hemoglobin concentration associated with spontaneous hemodynamic oscillations at tissue in a predetermined area of a human subject;
    polarizing the light to a polarized state such that the polarized light in the polarized state diffuses into the tissue in the predetermined area at a predetermined depth and the polarized light is maintained in the polarized state at the polarized depth;
    discriminating the light maintained in the polarized state and at the predetermined depth and generating a plurality of frames of the tissue in the predetermined area at the predetermined depth;
    acquiring the plurality of frames;
    selecting a region of interest having the same coordinates for each of the plurality of frames;
    averaging the number of pixels within each region of interest to create a raw reference signal;
    detrending the raw reference signal to create a detrended raw reference signal;
    performing frequency domain analysis of the detrended raw reference signal;
    identifying a frequency band of interest associated with the spontaneous hemodynamic oscillations;
    performing an inverse fast Fourier transform within the frequency band of interest to generate a reference signal indicative of blood volume oscillations at a selected spontaneous hemodynamic oscillation;
    for each sample of the reference signal at a predetermined point in time, multiplying the sample by each pixel of a frame at the same predetermined point in time to generate a three-dimensional coordinate matrix including a plurality of correlation matrix frames at each predetermined point in time; and
    adding the plurality of correlation matrix frames at each predetermined point in time to generate a two-dimensional hemodynamic map indicative of the strength of the spontaneous hemodynamic oscillation to assess the viability of the tissue in the predetermined area.

12. The method of claim 11 in which adding the plurality of correlation matrix frames at each predetermined point in time to generate a two-dimensional hemodynamic map indicative of the strength of the spontaneous hemodynamic oscillation assess the viability of other hemodynamic parameters including one or more of: heart rate, resting heart rate, heart rate variability, and tissue saturation for patients suffering from diminished blood circulation.

13. The method of claim 11 in which the spontaneous hemodynamic oscillations have a frequency in the range of 0.05 Hz to about 1.5 Hz.

14. The method of claim 11 in which the predetermined wavelength is in the range of about 500 nm to about 1,000 nm.

15. The method of claim 11 in which the predetermined depth is in the range of about 0.1 mm to about 0.5 mm.

16. The method of claim 11 in which the predetermined area includes a burn area of the human subject.

17. The method of claim 11 in which the predetermined area includes a wound area of a human subject.

* * * * *